(12) United States Patent
Nichols

(10) Patent No.: US 10,076,640 B2
(45) Date of Patent: Sep. 18, 2018

(54) TORQUE DEVICE

(71) Applicant: VANDERBILT UNIVERSITY, Nashville, TN (US)

(72) Inventor: Michael Nichols, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 15/234,883

(22) Filed: Aug. 11, 2016

(65) Prior Publication Data
US 2017/0043136 A1    Feb. 16, 2017

Related U.S. Application Data

(60) Provisional application No. 62/203,473, filed on Aug. 11, 2015.

(51) Int. Cl.
*A61M 25/09* (2006.01)

(52) U.S. Cl.
CPC ............ *A61M 25/09041* (2013.01); *A61M 2025/09116* (2013.01)

(58) Field of Classification Search
CPC ............ A61M 25/09041; A61M 2025/09116
See application file for complete search history.

(56) References Cited

U.S. PATENT DOCUMENTS

| | | | | |
|---|---|---|---|---|
| 4,261,375 A * | 4/1981 | Anderson | | A45D 2/12 132/224 |
| 4,739,151 A * | 4/1988 | Smal | | A45D 1/04 219/225 |
| 4,867,185 A * | 9/1989 | Clingen | | A45D 2/22 132/224 |
| 4,917,078 A * | 4/1990 | Zaborowski | | A45D 1/02 126/409 |
| 5,119,846 A * | 6/1992 | Tadrous | | A45D 2/24 132/223 |
| 5,711,324 A * | 1/1998 | Johnson | | A45D 2/24 132/245 |
| 6,213,140 B1 * | 4/2001 | Ploeger | | F16K 7/06 137/1 |
| 2002/0066460 A1 * | 6/2002 | Johnson | | A41G 5/0086 132/200 |
| 2004/0031501 A1 * | 2/2004 | Walsh | | A45D 2/40 132/225 |

(Continued)

*Primary Examiner* — Sean Dougherty
(74) *Attorney, Agent, or Firm* — Nixon Peabody LLP; Eduardo J. Quiñones

(57) ABSTRACT

A device for manipulating a wire includes a first structure and a second structure pivotably mounted with respect to each other so as to define respective facing surfaces configured for alternating between a closed position and at least one open position, where each of the respective facing surfaces includes one or more detent elements and one or more tooth elements extending therefrom. In the device, the tooth elements of the first structure and the second structure are in an interlocking and overlapping arrangement in at least the closed position. Further, each of the tooth elements has a concave surface for defining a passage between the facing surface in the at least one open position. Additionally, each of the detent elements is arranged to face the concave surface of one of the tooth elements of an opposite one of the respective facing surfaces in the closed position.

12 Claims, 16 Drawing Sheets

(56) References Cited

U.S. PATENT DOCUMENTS

| | | | |
|---|---|---|---|
| 2006/0174909 A1* | 8/2006 | Vestal | A45D 8/14 132/280 |
| 2009/0014024 A1* | 1/2009 | Wong | A45D 1/12 132/225 |
| 2009/0090379 A1* | 4/2009 | Potut | A45D 8/22 132/277 |
| 2016/0176057 A1* | 6/2016 | Troop | B26B 13/10 30/230 |

* cited by examiner

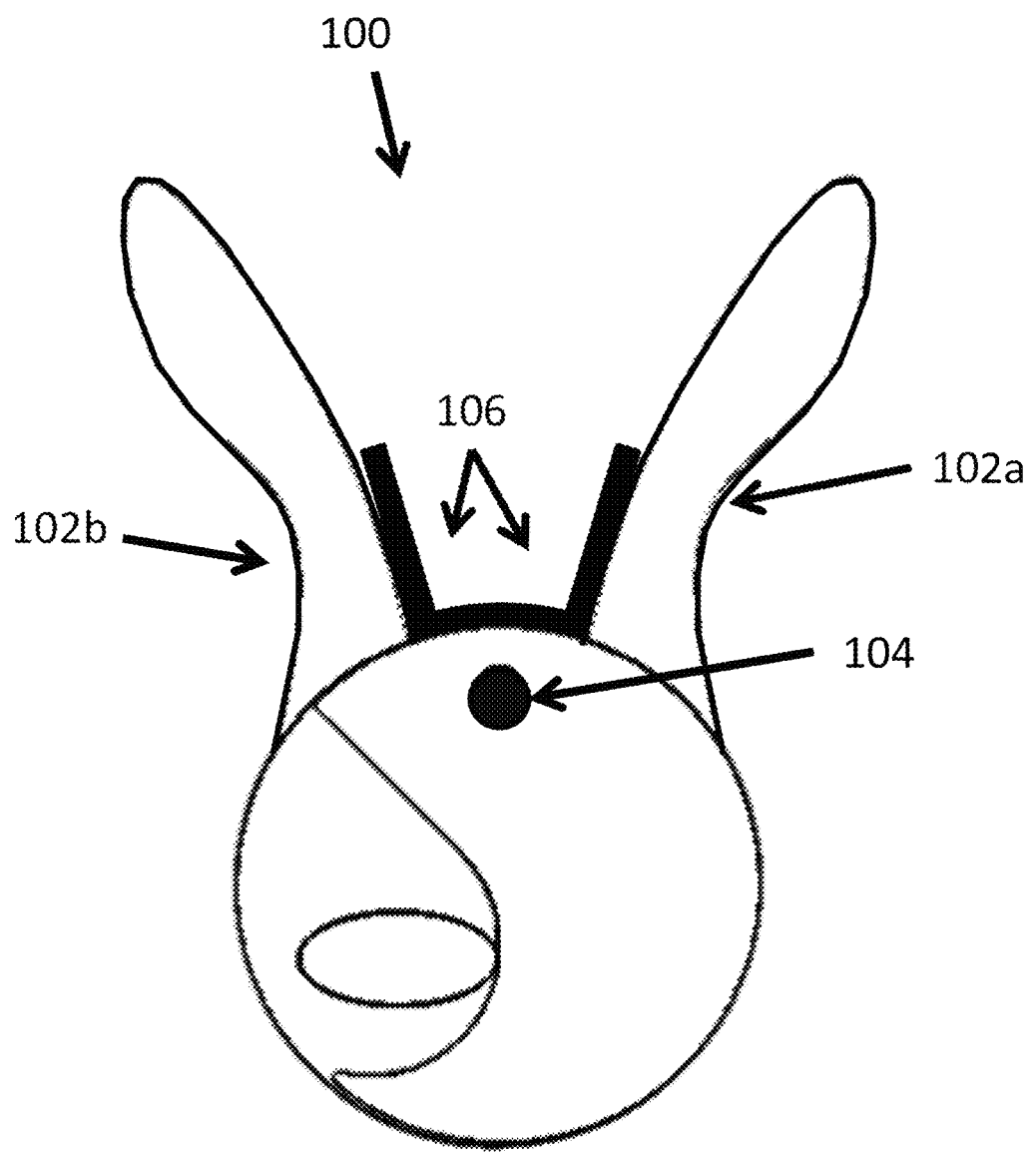

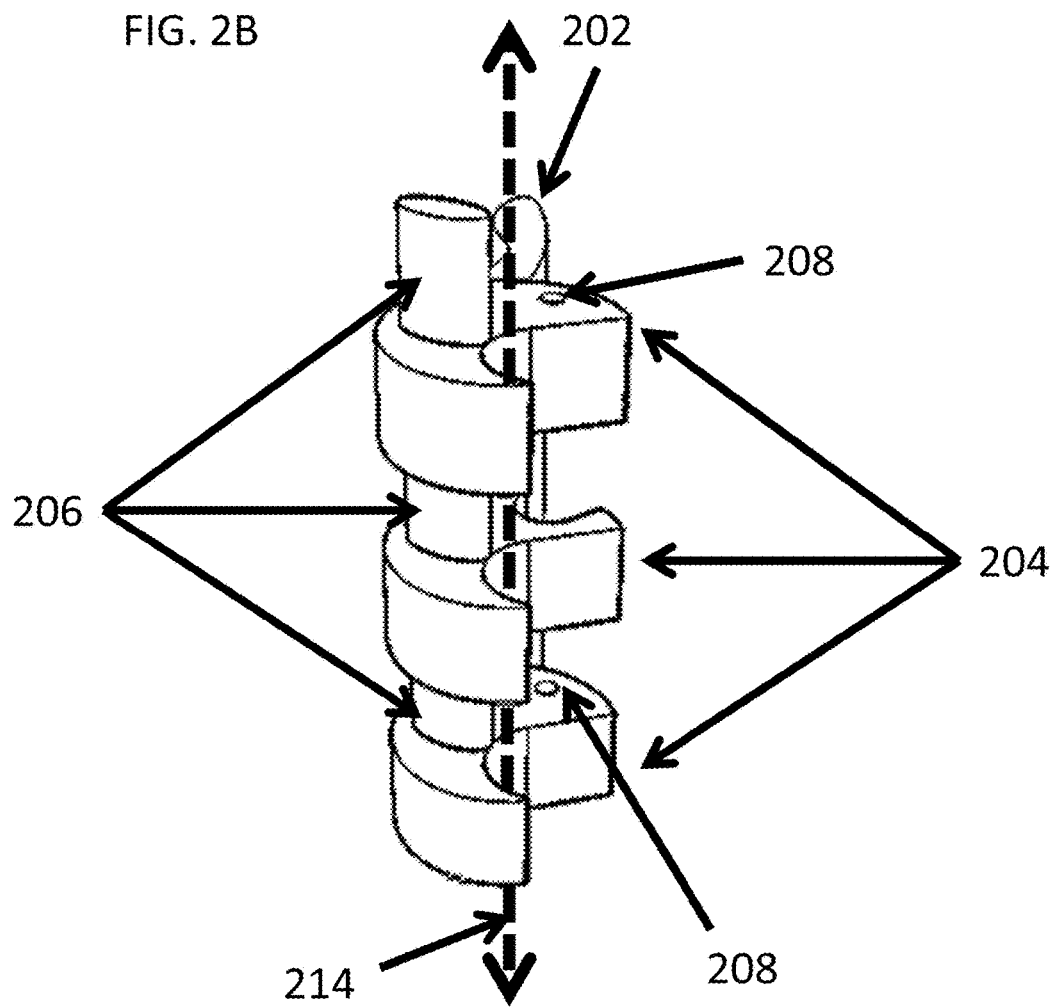

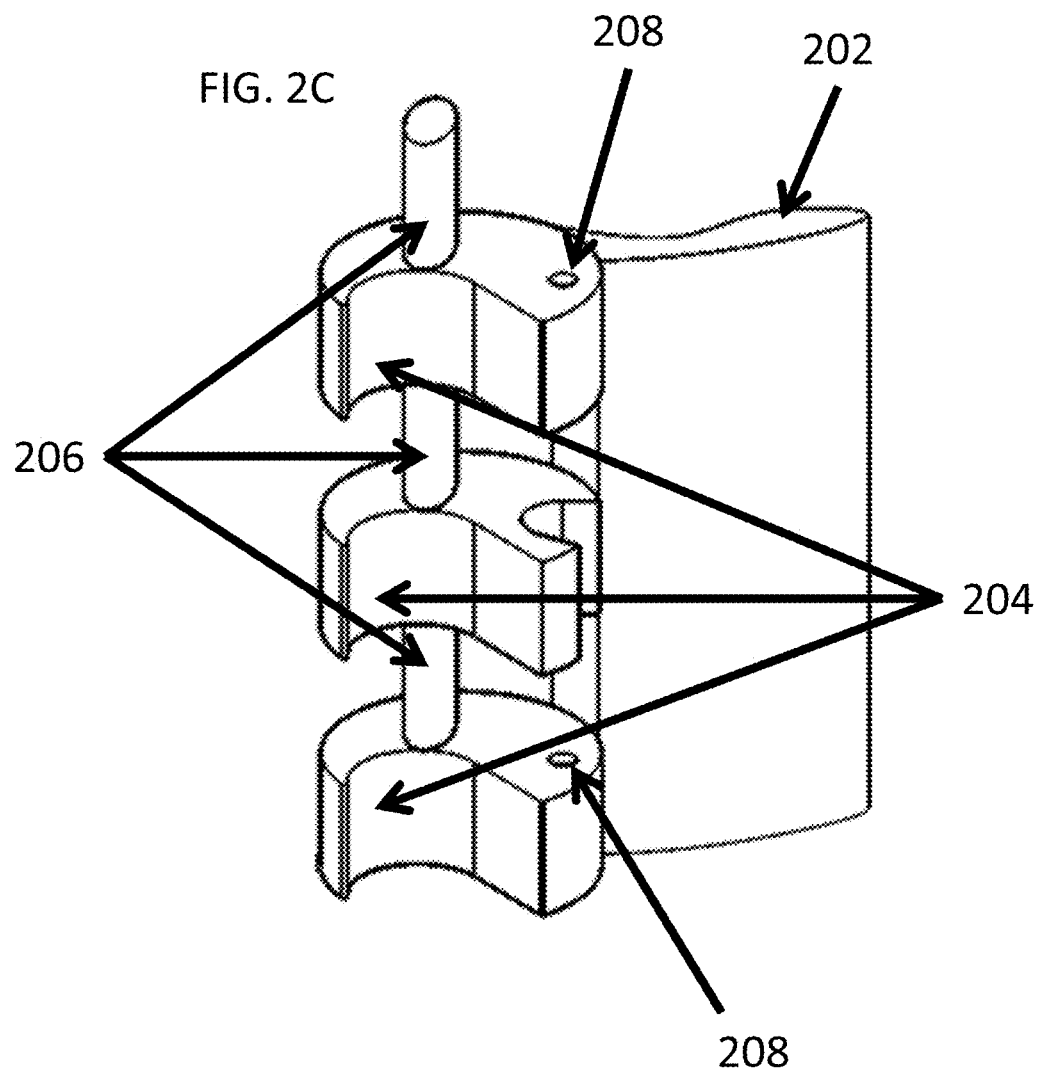

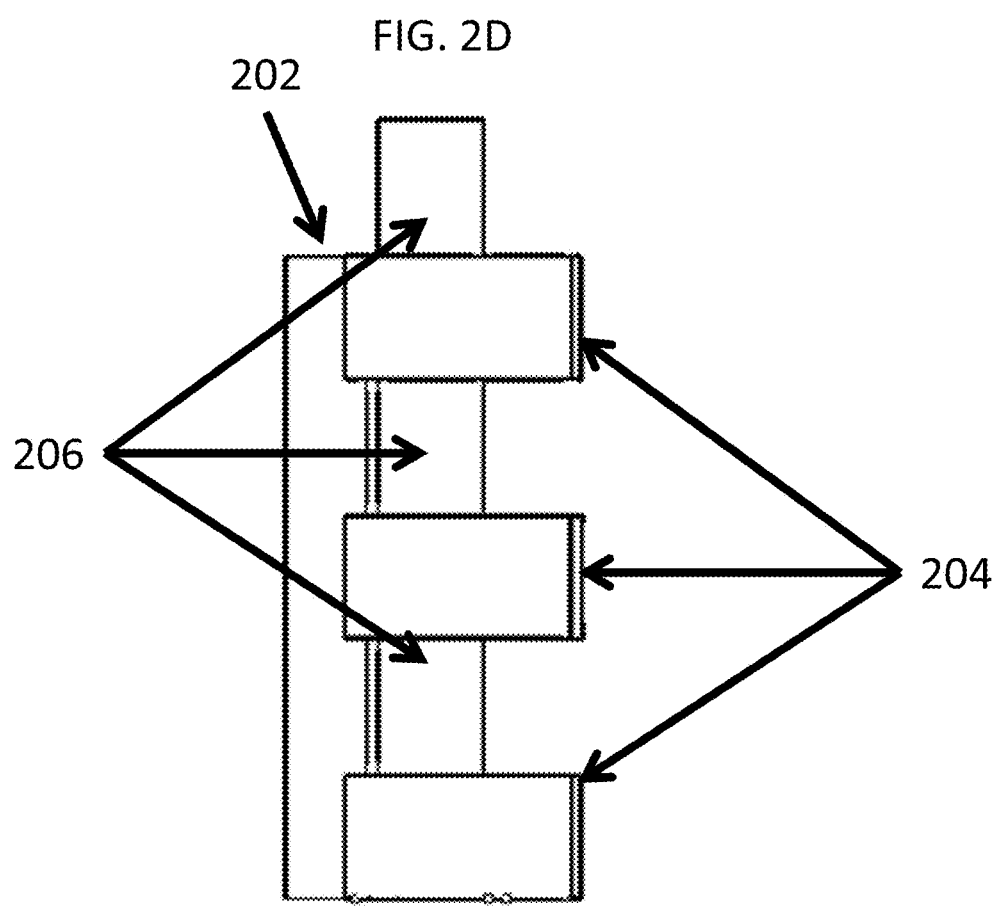

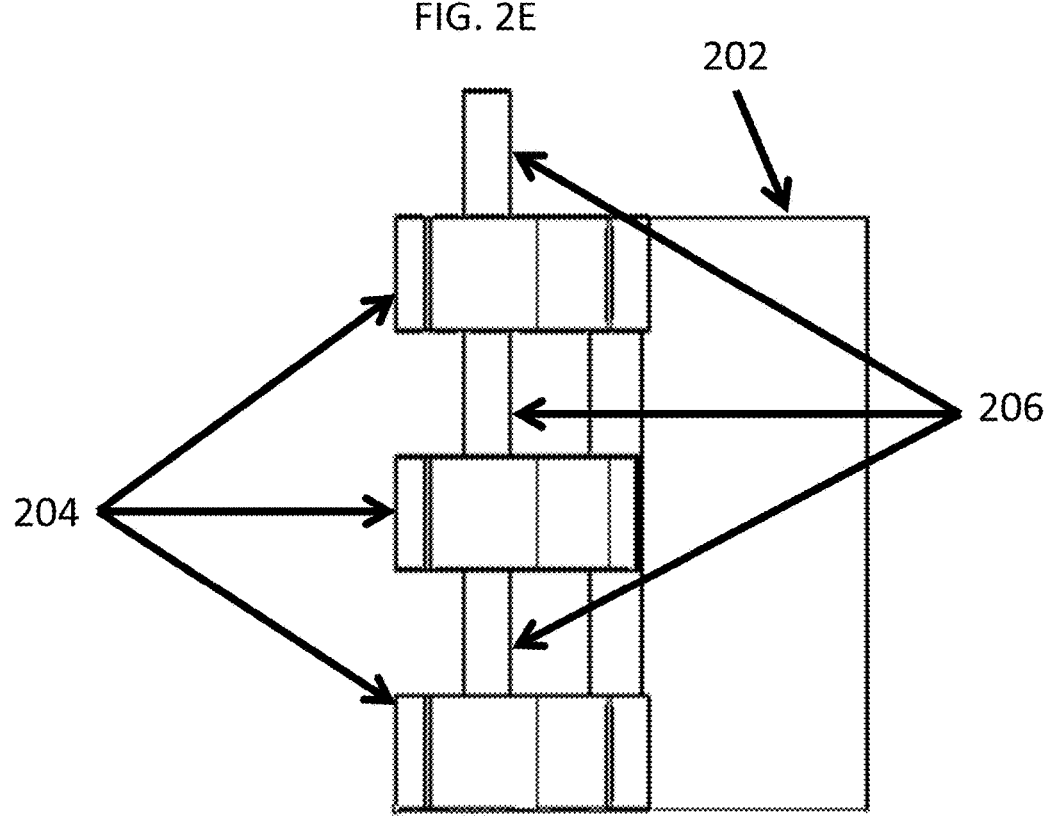

100 →

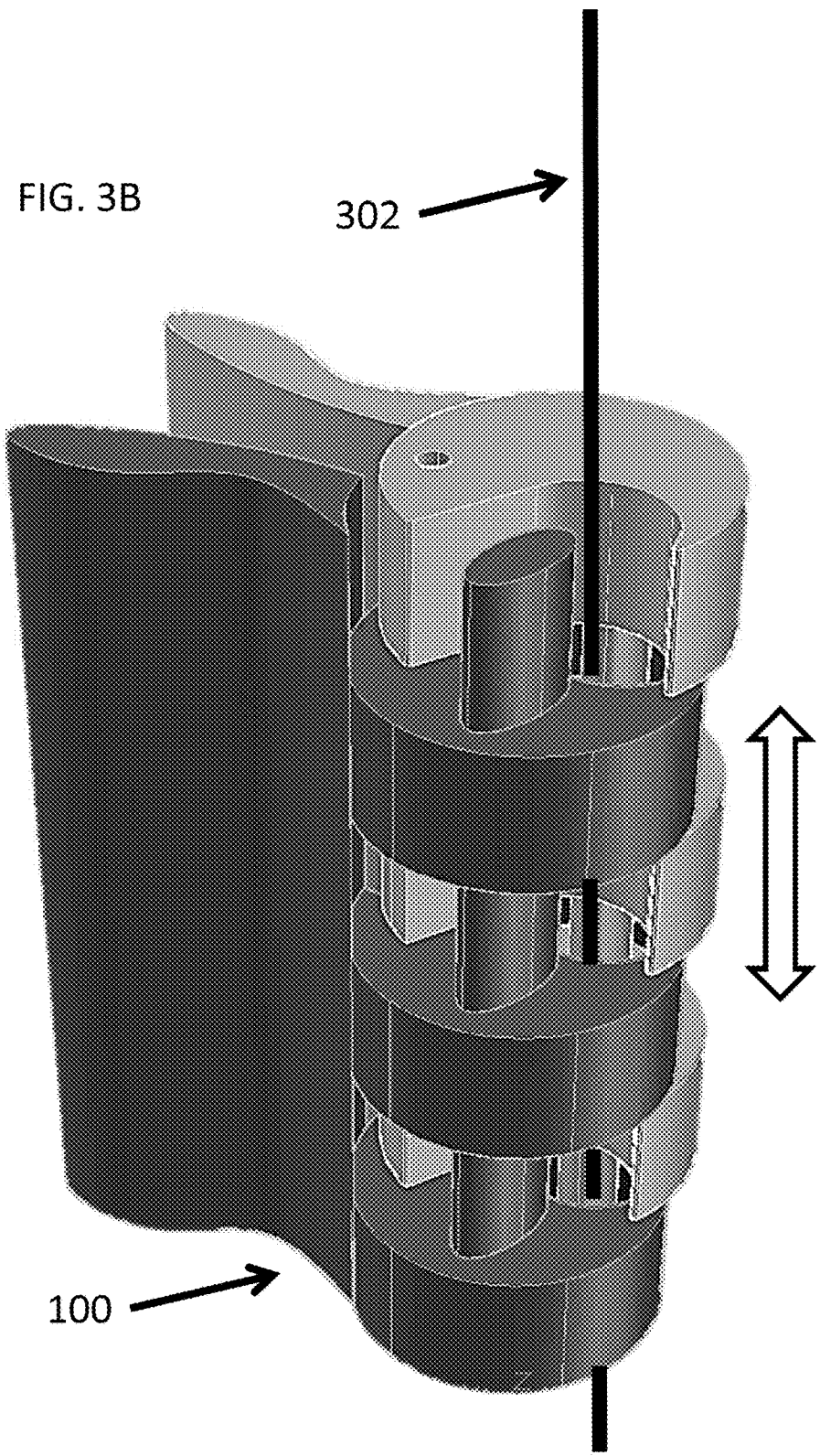

502

502

FIG. 8A
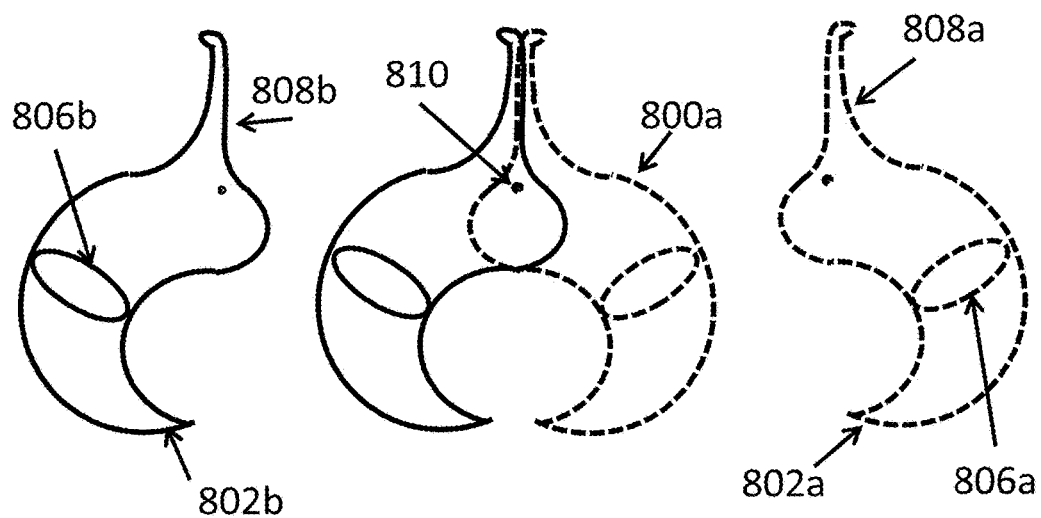
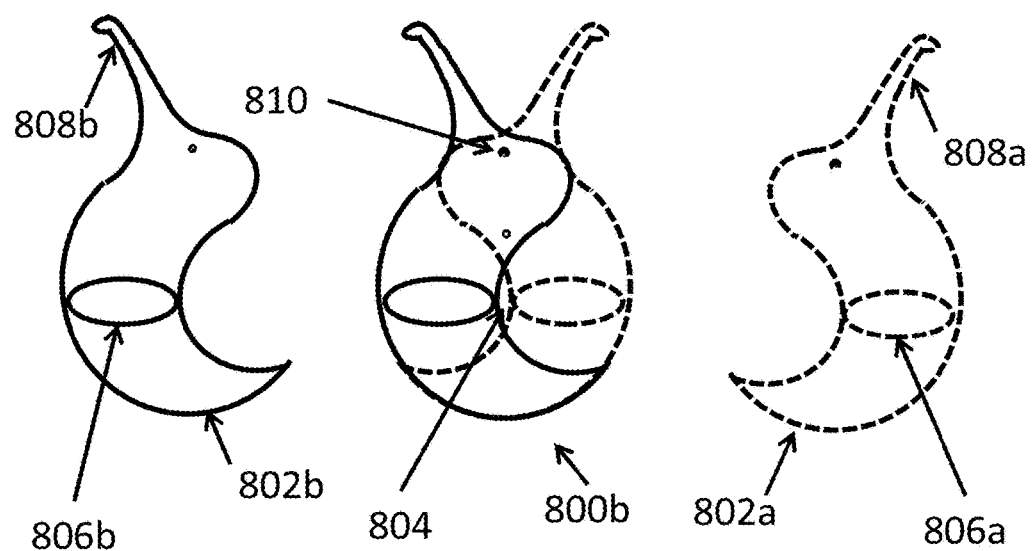
FIG. 8B

TORQUE DEVICE

CROSS-REFERENCE TO RELATED APPLICATIONS

This application claims priority to and the benefit of U.S. Provisional Patent Application No. 62/203,473, entitled "Torque Device 1" and filed Aug. 11, 2015, the contents of which are hereby incorporated by reference in their entirety as if fully set forth herein.

FIELD OF THE INVENTION

The present invention relates generally to torque devices for manual manipulation of a guidewire in medical applications.

BACKGROUND

Medical guidewires are commonly used for a variety of medical procedures. Such procedures include angioplasty, stenting, pacemaker insertion, electrophysiology studies, atherectomy, and thrombolysis and other coronary and peripheral endovascular procedures, and in endourology and therapeutic endoscopy of the gastrointestinal system. To position a guidewire at a desired location within a patient a medical professional navigates the guidewire through the patient's anatomy by manipulating the guidewire. Such manipulation includes advancing of the guidewire into a patient's vasculature or other portion of the patient's body while torqueing (i.e., twisting or rotating) the guidewire. Torqueing the guidewire allows the medical professional to change the spatial orientation of the tip of the guidewire when negotiating turns and branches in the patient's vasculature or other relevant portion of the patient's anatomy.

To manipulate the guidewire, medical professionals have traditionally used torque devices that securely grasp the guidewire to ease manipulation of the guidewire, but such devices typically require constant repositioning. For example, as a guidewire is advanced into the patient's body, the distance between the patient's body and the torque device decreases. When the proximity between the patient's body and the torque device decreases to the point that no further advancement is possible or difficult, repositioning is required. Typically, this involves the medical professional loosening the torque device, repositioning the torque device proximally along the guidewire to provide an additional length of guidewire between the patient's body and the torque device, and then retightening of the torque device to secure its position along the length of the guidewire. The process of loosening and repositioning the torque device may be repeated several times during the placement of the guidewire in to the patient.

Commercially-available torque devices typically require a two-handed operation to properly reposition the torque device. However, due to the complexities of some guidewire placement procedures, it may be inconvenient or even impractical for a practitioner to utilize both hands to reposition the torque device along the length of the guidewire. For example, if guidewire placement is critical, it may be undesirable to allow the guidewire to lie unheld during the repositioning procedure. As a result, additional care and attention may be required when manipulating the torque device relative to the guidewire during the procedure. This can lengthen the amount of time and the degree of difficulty necessary to complete the guidewire placement procedure.

An additional complexity with conventional torque devices is that their operation is typically not intuitive, leading to misuse of the torque device and inadvertent damage to the guidewire. Thus, some torque devices can require specialized training to facilitate proper usage of the device, yet still not avoid inadvertent misuse of the device during the course of the procedure. Additionally, some devices do not provide adequate gripping of the guidewire as may be required to push the guidewire through a vascular lesion or other guidewire path occlusion. Where an occlusion is encountered, the practitioner may overtighten the device in a manner that causes damage to the guidewire.

SUMMARY

The present invention is directed to a torque device for a medical guidewire that allows for one-handed operability, improved gripping, and which avoids improper usage and/or damage to the guidewire.

The various embodiments are directed to device for manipulating a wire. In one embodiment the device includes a first structure and a second structure pivotably mounted with respect to each other so as to define respective facing surfaces configured for alternating between a closed position and at least one open position, where each of the respective facing surfaces includes one or more detent elements and one or more tooth elements extending therefrom.

In the device, the tooth elements of the first structure and the second structure are in an interlocking and overlapping arrangement in at least the closed position. Further, each of the tooth elements has a concave surface for defining a passage between the facing surface in the at least one open position. Additionally, each of the detent elements is arranged to face the concave surface of one of the tooth elements of an opposite one of the respective facing surfaces in the closed position.

In some configurations, the detent elements and the tooth elements are arranged in an alternating series.

In some configurations, each of the detent elements in each of the respective facing surfaces extends no further than an edge of the concave surface of the tooth elements of the same one of the respective facing surfaces.

In the device, the shape of the concave surface can be continuous or discontinuous, which curved edges, straight edges, or any combination thereof.

The device can also include an elastic member arranged to hold the respective facing surfaces in a closed position in the absence of an external force.

The device can also include at least one ear associated with each of the first structure and the second structure In some configurations, each of the tooth elements is a substantially circular member with a cutout defining the concave surface.

In some configurations, a portion of an innermost edge of each of the detent elements is arranged to contact the concave surface of the one of the tooth elements of the opposite one of the respective facing surfaces in the closed position.

In some configurations, a shape of the innermost edge of each of the detent elements is substantially curved.

BRIEF DESCRIPTION OF THE DRAWINGS

FIG. 1 illustrates a torque device according to an embodiment of the invention;

FIGS. 2A, 2B, 2C, 2D, and 2E are different views a comb structure of the torque device of FIG. 1;

FIGS. 3A, 3B, and 3C are isometric views of the torque device of FIG. 1;

FIGS. 8A and 8B are detailed views of the operation of an alternate configuration for a torque device according to the invention.

DETAILED DESCRIPTION

Figure 2A:
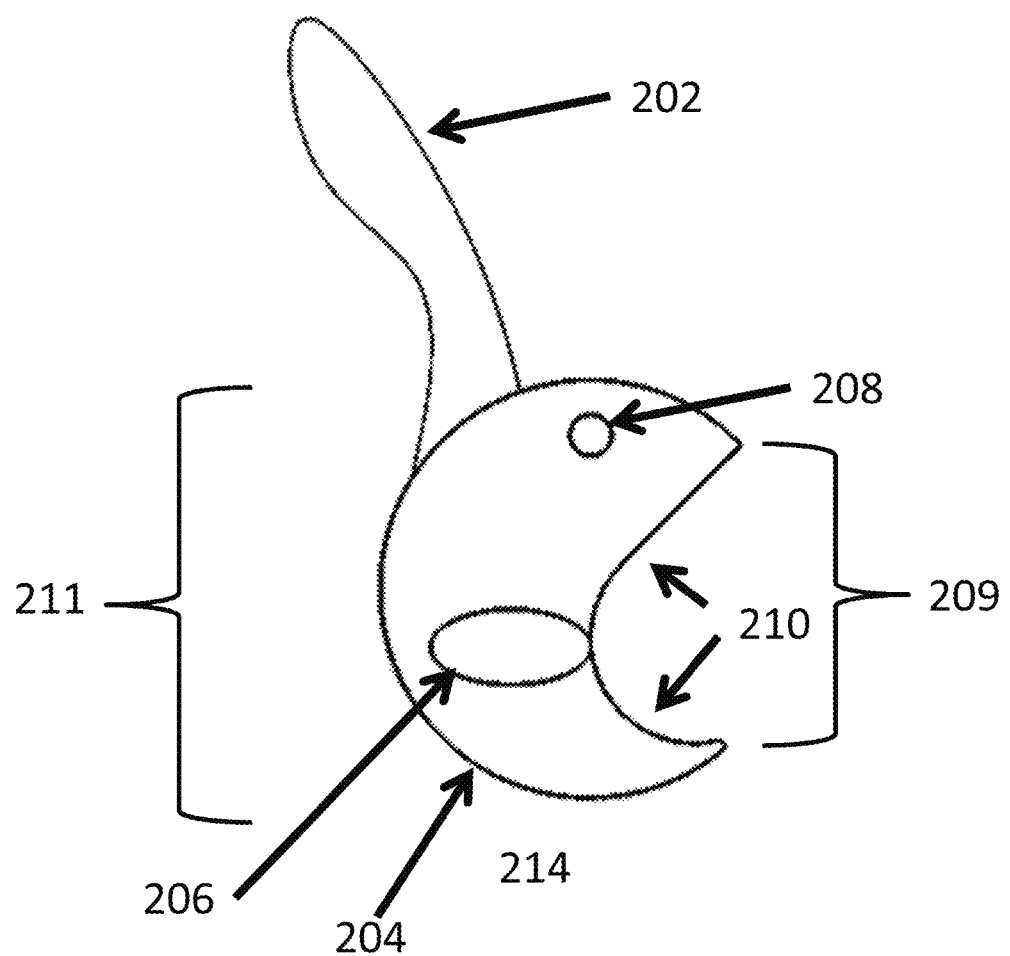

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The various embodiments of the invention are directed to improved torque devices for manual manipulation of a guidewire in various applications, such as medical applications. A torque device 100 according to an embodiment of the invention is shown in FIG. 1.

As shown in FIG. 1, the torque device 100 includes a first comb structure 102a and a second comb structure 102b. These elements are pivotably mounted with respect to each other as shown in FIG. 1, a pin 104 can be provided to join comb structures 102a and 102b and to allow the pivoting of the comb structures with respect to each other. Additionally, a spring element 106 can be provided to apply a restorative force for the comb structures when they are pivoted with respect to each other. However, any other type of device applying a restorative force to bring comb structure 102a and 102b together can be used in the various embodiments.

Now turning to FIGS. 2A, 2B, 2C, 2D, and 2E, there are various views shown of each of the comb structures 102a and 102b of FIG. 1. As shown in FIGS. 2A-2E, each of the comb structures includes a handle or ear portion 202, a plurality of tooth elements 204 extending from the ear portion 202, and a plurality of detents 206 connecting the tooth elements 204 to each other. As shown in FIGS. 2A-2E, the number of the tooth elements 204 and the number of the detents 206 is the same, but it is not necessary. Further, the tooth elements 204 and the detents 206 are arranged in an alternating sequence.

As shown in FIGS. 2A-2E, each of the plurality of tooth elements 210 is shown as being substantially circular with cutouts defining concave surfaces 210 for the facing surfaces 209 of the tooth elements 204. Further, the concave surfaces 210 are arranged in the plurality of tooth elements 204 so that that they define a passage or channel 214 though the plurality of tooth elements 204. For example, as shown in FIGS. 2A-2E, the cutouts for the concave surfaces 210 are arranged in parallel. As shown in FIGS. 2A-2E, the cutouts defining the concave surfaces are, at least in part curved. However, in the various embodiments other types of cutout shapes are possible, as illustrated in further detail below.

As also shown in FIGS. 2A-2E, the plurality of detents 206 are arranged so that innermost surfaces, with respect to a corresponding one of the facing surfaces 209 of another comb structure, are disposed along at or near an edge of the cutouts, i.e., along an edge of the concave surfaces 210. Although the detents 206 are illustrated in FIGS. 2A-2E as having an oval cross-section shape, the detents can be of any shape in the various embodiments.

As further shown in FIGS. 2A-2E, the comb structures 102a and 102b can include pin holes 208 or grooves 212 to allow the pin 104 to extend there thru.

Thus, in operation, the spring 104 pushes the facing surfaces 209 for each of comb structures 102a and 102b towards each other to provide a closed configuration. Thus, a wire disposed between the comb structures 102a and 102b can be held in place. If additional force is needed to hold such a wire in place, the user can apply pressure to the outside faces 211 of each of comb structures 102a and 102b. To provide an open configuration, a user can push ears 202 towards each other to separate the facing surfaces of comb structures 102a and 102b. In the various embodiments, the torque device 100 can have any number of open configurations by adjusting the amount of pressure applied via ears 202. Thus, this allows the grip of the torque device 100 to be loosened partly, to allow a controlled reposition of the torque device 100 relative to the wire, or completely to allow the torque device 100 to be completely removed. Notably, this arrangement allows for one-handed operation.

In some configurations, a device can be used to limit the range of rotation of the comb structures. For example, a screw can be used to adjust how close the ears come to each other. However, the various embodiments are now limited in this regard and other devices can be incorporated to limit the amount of rotation.

Figure 3A:
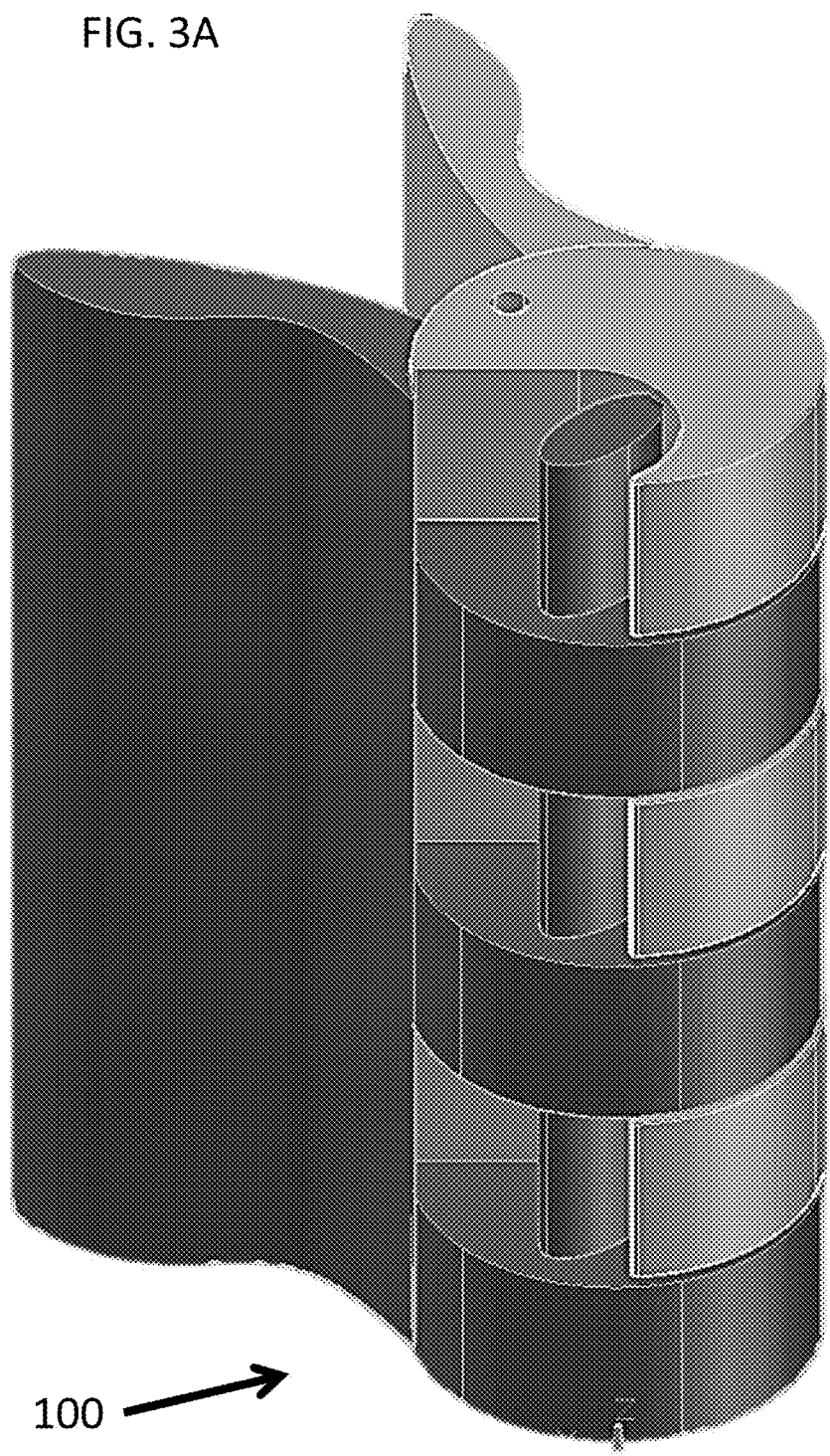
Figure 3C:
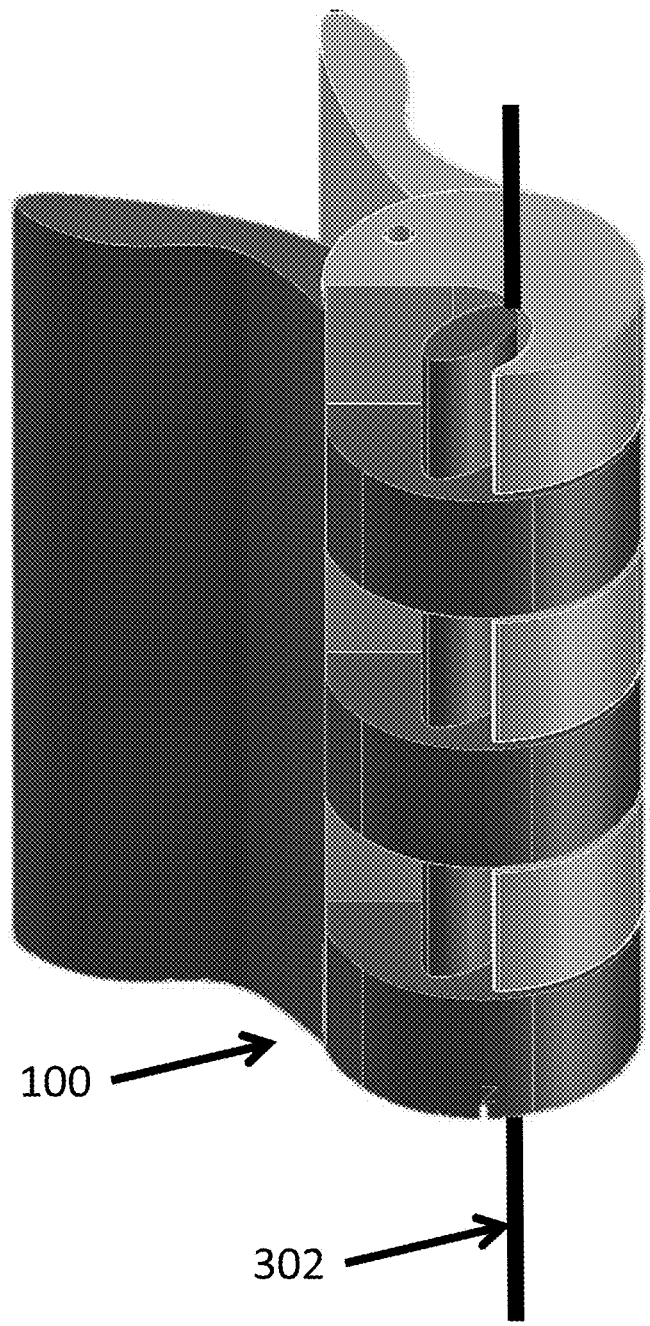

FIGS. 3A-3C show various isometric views of torque device 100 of FIG. 1 to illustrate its operation, including a closed configuration (see FIG. 3A), a partly open configuration for repositioning the torque device with respect to a length of a wire 302 (where tooth elements 204 at a distal end of device 100 still overlap, at least partly; see FIG. 3B), and a closed and grasping configuration for holding a wire 302 (see FIG. 3C).

Figure 4A:
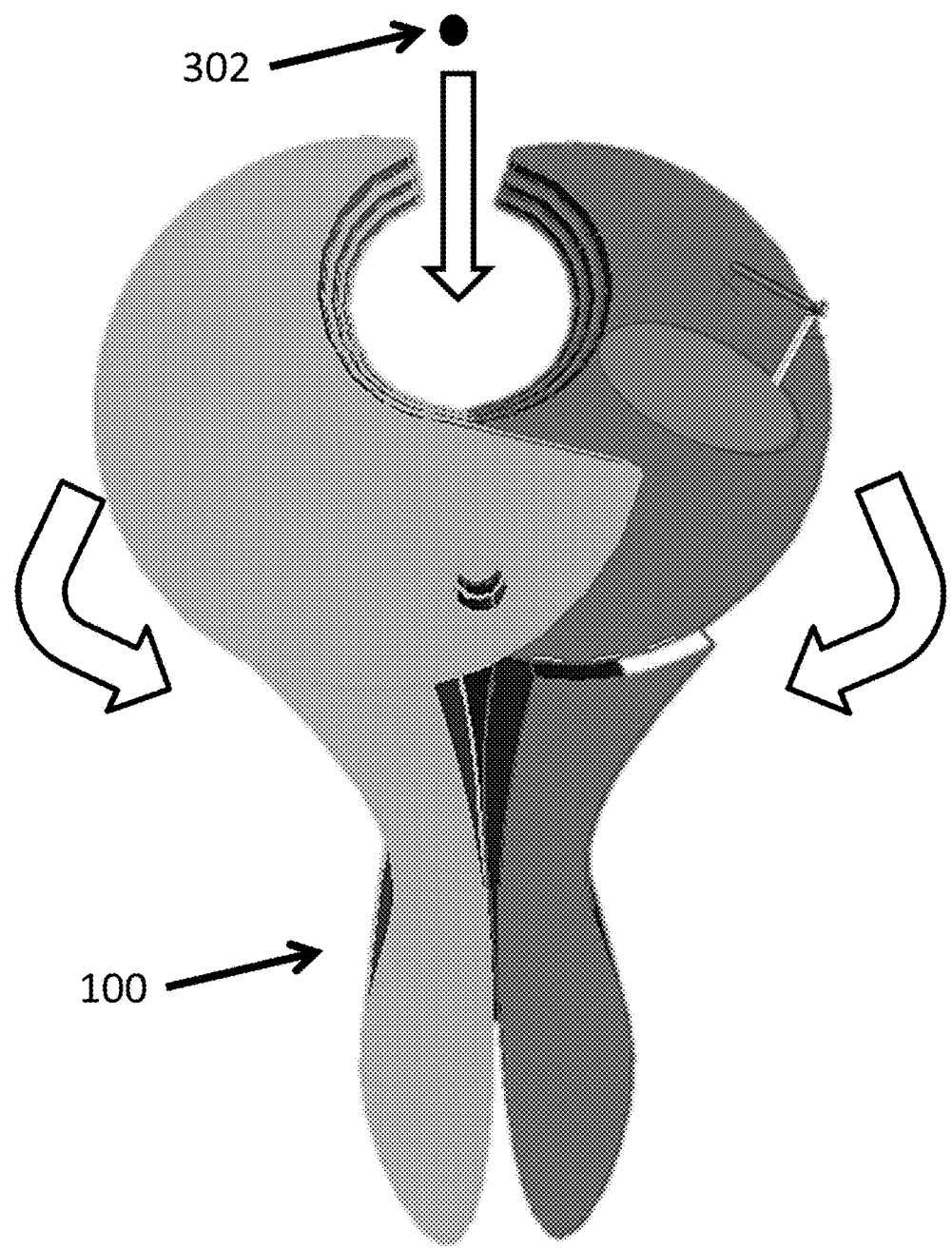
FIGS. 4A, 4B, and 4C are side views of the torque device of FIG. 1.
Figure 4B:
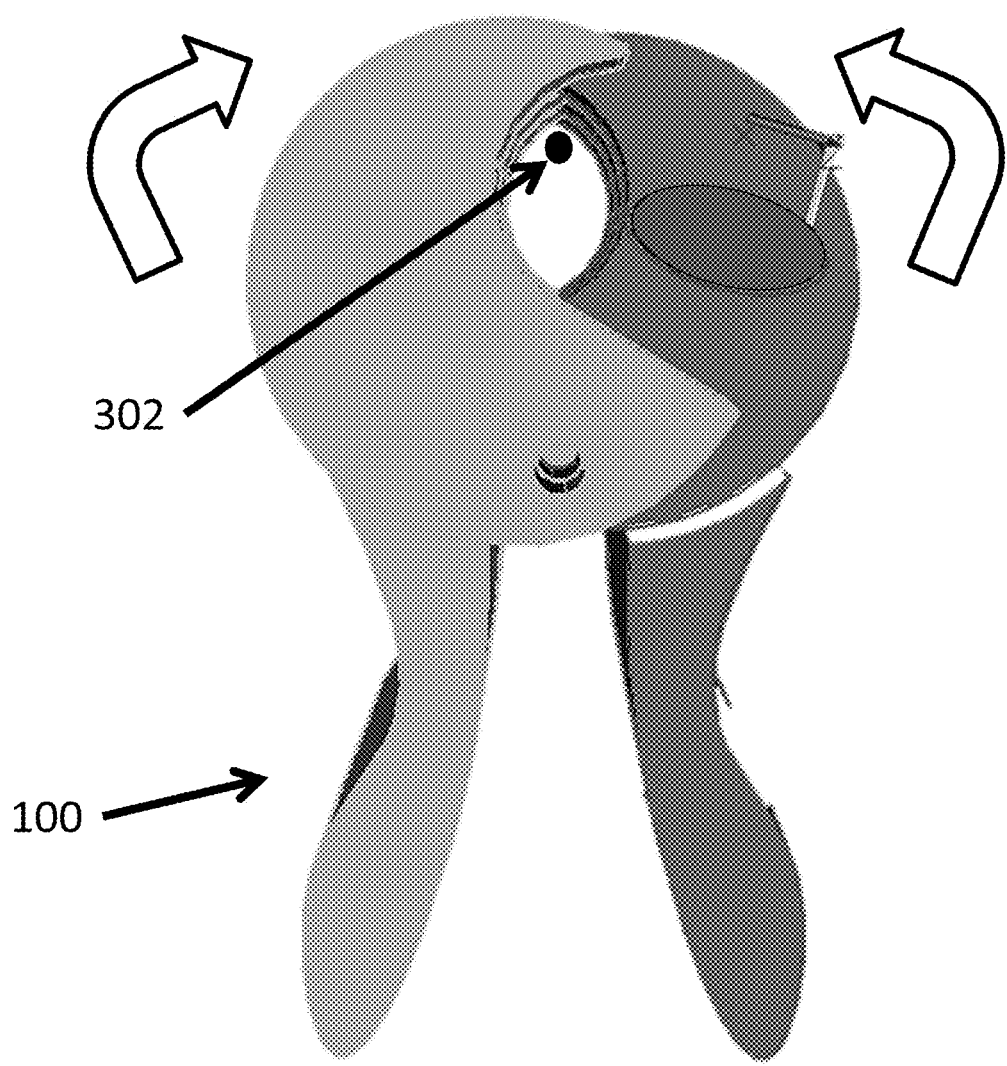
Figure 4C:
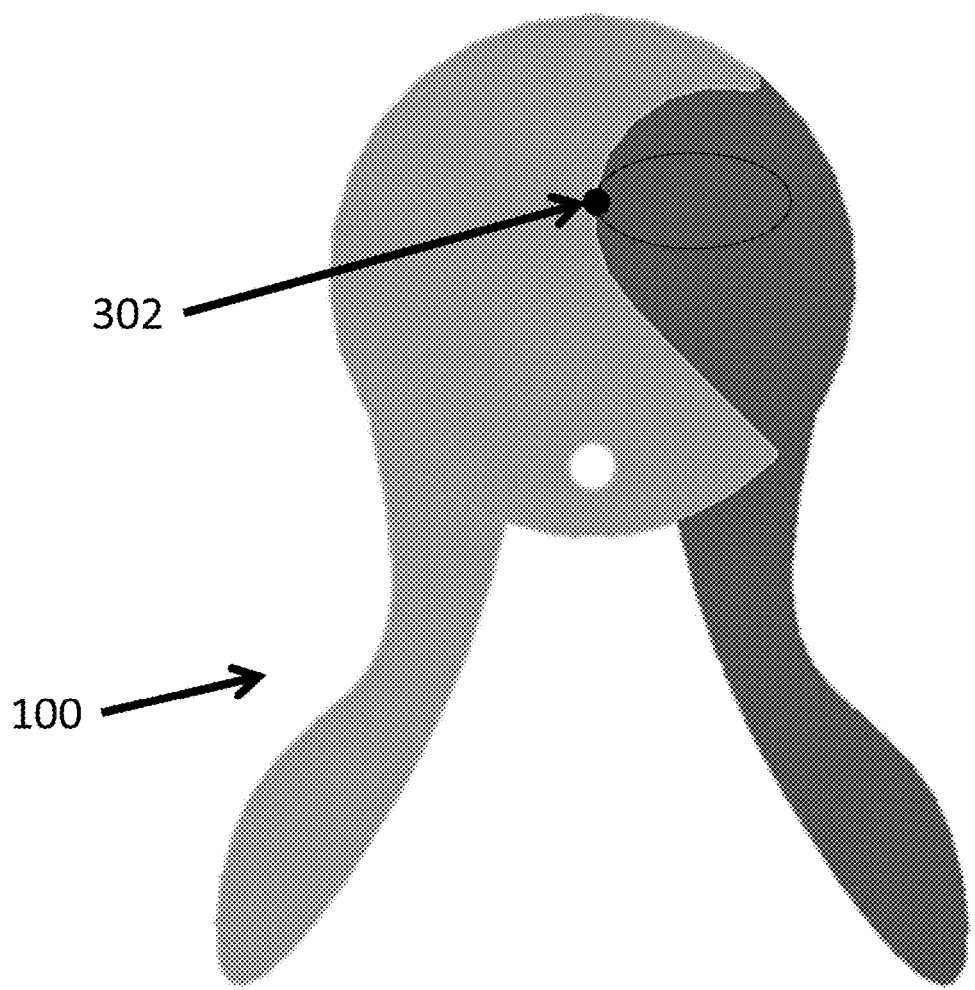

For initially grasping the wire, it is possible to use a completely open configuration, as illustrated in FIGS. 4A-4C. FIGS. 4A-4C show various side views of torque device 100 of FIG. 1 to illustrate its operation, including a complete open configuration, where the tooth elements 204 do not overlap to allow torque device 100 to be positioned for grasping with respect to wire 302 (see FIG. 4A), a partly closed configuration initiate grasping of wire 302 (where tooth elements 204 at a distal end of device 100 overlap, at least partly; see FIG. 4B), and a closed and grasping configuration for holding the wire 302 (see FIG. 4C).

As shown in the preceding figures, the plurality of tooth elements and the plurality of detents are arranged in series in an alternating sequence, wherein a number of the plurality of tooth elements and a number of the plurality of detents are the same. Such a configuration is provided so that the plurality of detents and the plurality of tooth elements are arranged so that, in the closed configuration, the concave surfaces for the plurality of tooth elements of each one of the first and the second comb structures rests on or contacts an innermost edge one of the plurality of detents for the other one of the first and the second comb structures. For example, as shown in FIG. 1 and as further shown below. In this way, pressure on the wire is evenly provided along the length grasped by the torque device, avoiding damage to the wire.

Figure 5A:
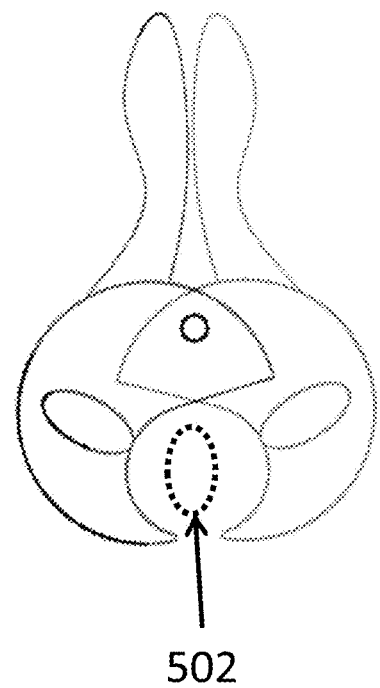
FIGS. 5A and 5B are detailed views of the operation of the torque device of FIG. 1.
Figure 5B:
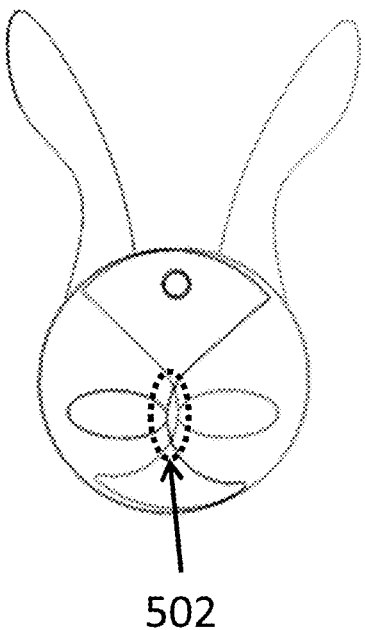

FIGS. 5A and 5B illustrate the torque device 100 in open (100a) and closed (100b) configurations, respectively. As shown in these figures, the channel or passages defined by the concave surfaces on each comb structure are arranged so that when the tooth elements are interdigitated and pivot from the open position to the closed position, the concave surfaces define a smaller passage 502 in which a wire would be held. Further, the concave surfaces can be arranged such that as the tooth elements are interlocked and pivot from the open position to the closed position, the wire is guided to the smaller passage.

Additionally, to maintain even pressure on the wire, the shape and locations of the detents and the facing surfaces of the tooth elements are carefully selected. In particular, as shown in FIGS. 5A and 5B, an innermost edge of the detents is arranged to line up with portion of the concave surfaces where the passage 502 is smallest. Alternatively stated, the shape and locations of the detents and the facing surfaces of the tooth elements are selected so that in the closed position, the innermost edge of each of the detents in one comb is in contact with a portion of the concave surfaces of the tooth elements of another comb while reducing the size of passage 502 as much as possible. As a result, a wire in passage 502 receives even pressure from both sides along its entire length.

Further, by selection of curved surfaces for the facing surfaces of the tooth elements, secure grasping is facilitated. That is, the scissor-type action of the curved facing surfaces of the tooth elements of the facing combs causes the wire to be guided to the passage, regardless of the wire's initial position between the combs, where pressure is evenly applied from opposite sides.

However, the various embodiments are not limited solely to the configuration described above. Rather, in other configurations, the configuration of the detents and/or the facing surfaces of the tooth elements can vary. This is illustrated in the following figures.

Figure 6A:
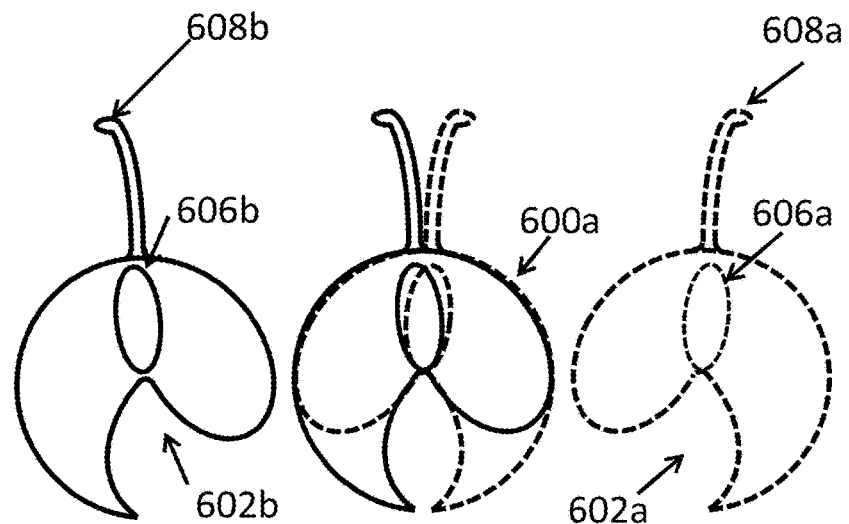
FIGS. 6A and 6B are detailed views of the operation of an alternate configuration for a torque device according to the invention.
Figure 6B:
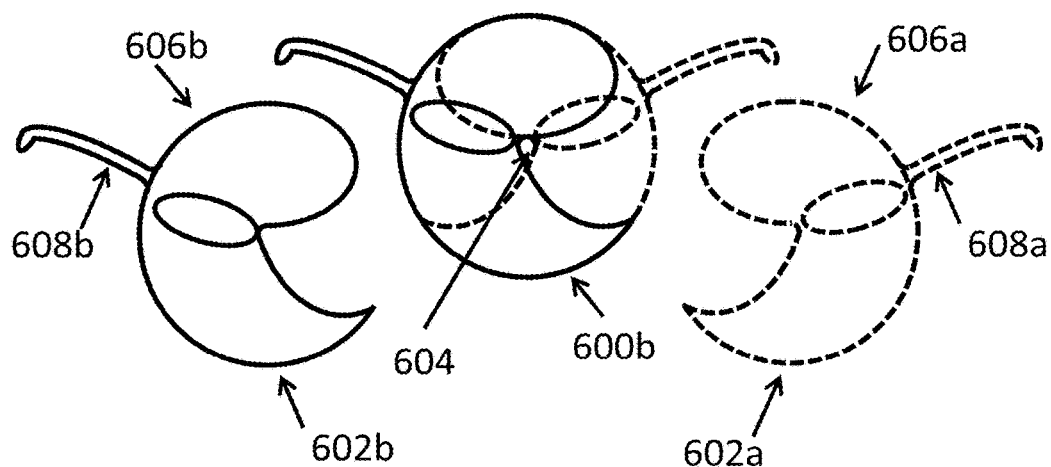

FIGS. 6A and 6B illustrate an alternate configuration of a torque device with comb structures 602a and 602b in accordance with the various embodiments in open (600a) and closed configurations (600b), respectively. In this configuration, rather than a curved, continuous concave surface, the concave surface is formed by two curves meeting at an apex, at which the passage 604 is formed. This configuration is also configured to have a center of rotation corresponding to apex, i.e, the passage defined by the two comb structures 602a and 602b in the closed configuration and allows 120 degrees of rotation. The detents 606a and 606b can be located adjacent to the apex to provide even pressure, as described above. Also, the placement of ears 608a and 608b is illustrated.

Figure 7A:
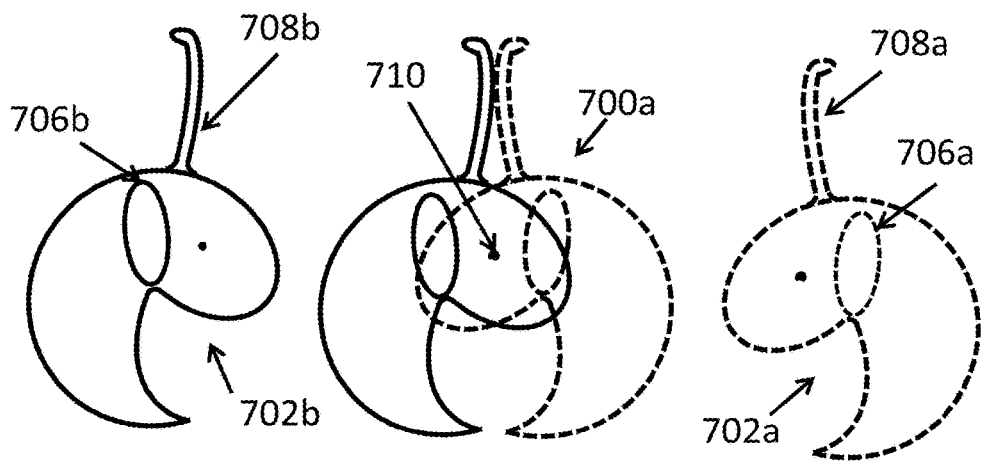
FIGS. 7A and 7B are detailed views of the operation of an alternate configuration for a torque device according to the invention.
Figure 7B:
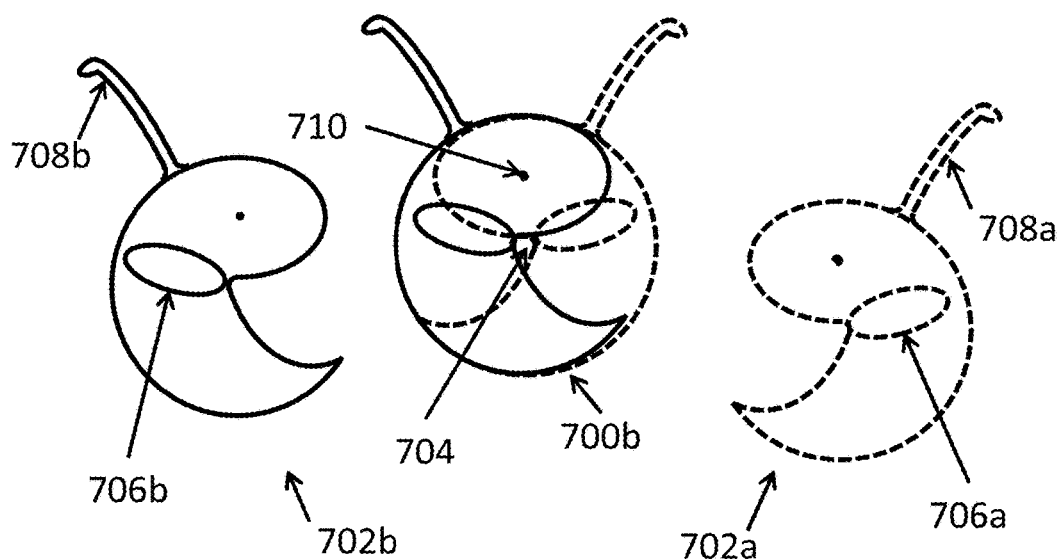

FIGS. 7A and 7B illustrate an alternate configuration of the torque device similar to that of FIGS. 6A and 6B, showing open (700a) and closed configurations (700b), respectively. In this configuration, rather than a curved, continuous concave surface, the concave surface is formed by two curves meeting at an apex, at which the passage 704 is formed between the two comb structures 702a and 702b. The detents 706a and 706b can be located adjacent to the apex to provide even pressure, as described above. Also, the placement of ears 708a and 708b is illustrated. However, unlike the configuration of FIGS. 6A and 6B, the center of rotation 710 is shifted from the apex. The amount of shift can be used to device the amount of rotation. In the configuration of FIGS. 7A and 7B, 70 degrees of rotation are permitted.

FIGS. 8A and 8B illustrate another alternate configuration of a torque device with comb structures 802a and 802b in accordance with the various embodiments in open (800a) and closed configurations (800b), respectively. In this configuration, a curved, continuous concave surface is provided at the inner faces of tooth elements, at which the passage 804 is formed in the closed configuration. This configuration is also configured to have a center of rotation 810 far from the passage defined by the two comb structures 802a and 802b in the closed configuration and allows 60 degrees of rotation. The detents 806a and 806b can be located adjacent to the passage to provide even pressure, as described above. Also, the placement of ears 808a and 808b is illustrated.

While various embodiments of the present invention have been described above, it should be understood that they have been presented by way of example only, and not limitation. Numerous changes to the disclosed embodiments can be made in accordance with the disclosure herein without departing from the spirit or scope of the invention. For example, although only curved surfaces are illustrated for the concave surfaces, linear surfaces can be provided such that the concave surfaces are polygonal. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A device for manipulating a wire, comprising:
a first structure and a second structure pivotably mounted with respect to each other so as to define respective facing surfaces configured for alternating between at least one closed position and at least one open position, each of the respective facing surfaces comprising one or more detent elements and one or more tooth elements extending therefrom,
wherein the tooth elements of the first structure and the second structure are in an interlocking and overlapping arrangement in the at least one closed position,
wherein each of the tooth elements each comprise a concave surface, and wherein the concave surface in each of the tooth elements of the first structure and the second structure are arranged to define a straight passage between the facing surfaces in at least one closed position, wherein the wire is configured to lie across each of the teeth elements of the first structure and the second structure in the at least one closed position, and
wherein each of the detent elements is arranged to face the concave surface of one of the tooth elements of an opposite one of the respective facing surfaces in the at least one closed position.

2. The device of claim 1, wherein the detent elements and the tooth elements are arranged in an alternating series.

3. The device of claim 1, wherein each of the detent elements in each of the respective facing surfaces extends no further than an edge of the concave surface of the tooth elements of the same one of the respective facing surfaces.

4. The device of claim 1, wherein a shape of the concave surface is continuous.

5. The device of claim 1, wherein a shape of the concave surface is a curved shape.

6. The device of claim 1, wherein a shape of the concave surface is discontinuous.

7. The device of claim 1, further comprising an elastic member arranged to apply a force against the first structure and the second structure so as to bias the respective facing surfaces towards the at least one closed position.

8. The device of claim 1, further comprising at least one ear associated with each of the first structure and the second structure.

9. The device of claim 1 wherein each of the tooth elements comprises a substantially circular member with a cutout defining the concave surface.

10. The device of claim 1, wherein a portion of an innermost edge of each of the detent elements is arranged to contact the concave surface of the one of the tooth elements of the opposite one of the respective facing surfaces in the closed position.

11. The device of claim 1, wherein a shape of the innermost edge of each of the detent elements is substantially curved.

12. The device of claim 1, wherein the tooth elements of the first structure and the second structure are in the interlocking and the overlapping arrangement in at least one of the open positions.

* * * * *